US012653797B2

(12) United States Patent (10) Patent No.: US 12,653,797 B2
Yamashita et al. (45) Date of Patent: Jun. 16, 2026

(54) TABLET AND METHOD FOR MANUFACTURING SAME

(71) Applicant: AYUMI PHARMACEUTICAL CORPORATION, Tokyo (JP)

(72) Inventors: Miki Yamashita, Kanagawa (JP); Yusuke Takigami, Kanagawa (JP)

(73) Assignee: AYUMI PHARMACEUTICAL CORPORATION, Tokyo (JP)

( * ) Notice: Subject to any disclaimer, the term of this patent is extended or adjusted under 35 U.S.C. 154(b) by 522 days.

(21) Appl. No.: 18/010,954

(22) PCT Filed: Jul. 2, 2021

(86) PCT No.: PCT/JP2021/025101
§ 371 (c)(1),
(2) Date: Dec. 16, 2022

(87) PCT Pub. No.: WO2022/004871
PCT Pub. Date: Jan. 6, 2022

(65) Prior Publication Data
US 2023/0255907 A1 Aug. 17, 2023

(30) Foreign Application Priority Data

Jul. 3, 2020 (JP) ................................ 2020-115271
Jan. 6, 2021 (JP) ................................ 2021-000629

(51) Int. Cl.
| | |
|---|---|
| *A61K 31/167* | (2006.01) |
| *A61K 9/20* | (2006.01) |
| *A61K 47/32* | (2006.01) |
| *A61K 47/38* | (2006.01) |

(52) U.S. Cl.
CPC .............. *A61K 31/167* (2013.01); *A61K 9/20* (2013.01); *A61K 47/32* (2013.01); *A61K 47/38* (2013.01)

(58) Field of Classification Search
CPC ........ A61K 31/167; A61K 9/20; A61K 47/32; A61K 47/38
See application file for complete search history.

(56) References Cited

U.S. PATENT DOCUMENTS

| | | | |
|---|---|---|---|
| 2015/0110880 A1 | 4/2015 | Sekiguchi et al. | |
| 2021/0186884 A1* | 6/2021 | Sakamoto | ............ A61K 9/2027 |

FOREIGN PATENT DOCUMENTS

| | | | |
|---|---|---|---|
| CN | 111343974 A | 6/2020 | |
| JP | 2013-216610 A | 10/2013 | |
| JP | 2015-63521 A | 4/2015 | |
| JP | 2017-210478 A | 11/2017 | |
| JP | 2018-58910 A | 4/2018 | |
| JP | 2018058910 * | 4/2018 | .............. A61P 25/28 |
| JP | 2018-90638 A | 6/2018 | |
| WO | WO-2019093434 A1 * | 5/2019 | .............. A61P 29/00 |

OTHER PUBLICATIONS

ISR and Written Opinion for PCT/JP2021/025101, dated Aug. 17, 2021 (w/ translation).
IPRP for PCT/JP2021/025101, Dec. 13, 2022 dated (w/ translation).
Office Action for CN App. No. 202180044916.5, dated Mar. 28, 2024 (w/ translation).
Office Action for CN App. No. 202180044916.5, dated Nov. 23, 2023 (w/ translation).

* cited by examiner

*Primary Examiner* — Sean M Basquill
(74) *Attorney, Agent, or Firm* — Greenblum & Bernstein, P.L.C.

(57) ABSTRACT

The present invention addresses the problem of providing a tablet that contains a high concentration of acetaminophen, satisfies an acetaminophen dissolution rate from the tablet of at least 80% in 15 minutes, and can be manufactured by dry direct compression. The present invention provides a tablet including: acetaminophen that has a median particle diameter in a range from 100 to 350 μm; crystalline cellulose that has a bulk density in a range from 0.10 to 0.23 g/cm$^3$; and at least two types of disintegrants. The at least two types of disintegrants are (a) at least one disintegrant selected from the group consisting of crospovidone, croscarmellose sodium, and sodium starch glycolate, and (b) a disintegrant that is a low-substituted hydroxypropyl cellulose. The acetaminophen content per tablet is at least 86 weight %.

4 Claims, 2 Drawing Sheets

[Figure 1]
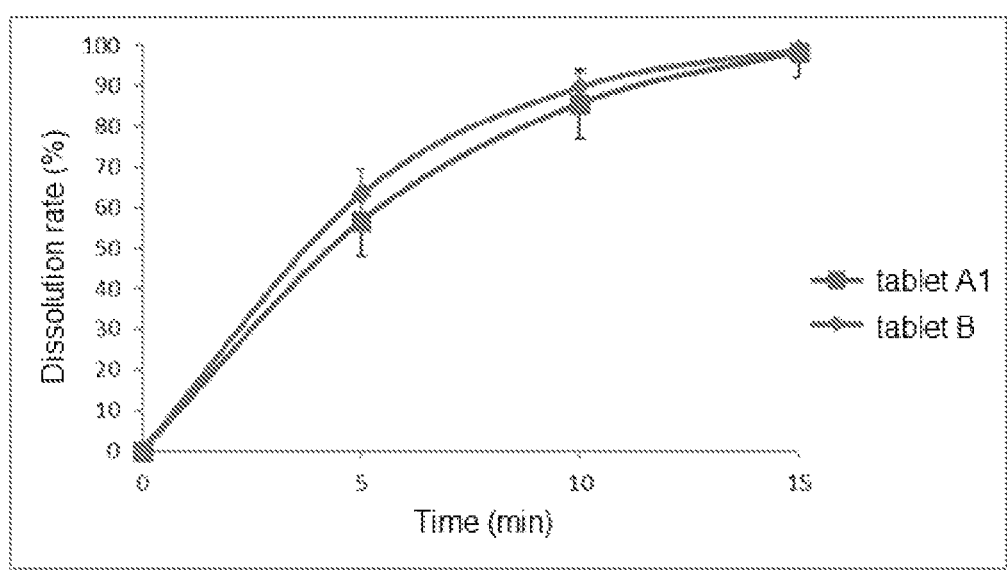
[Figure 2]
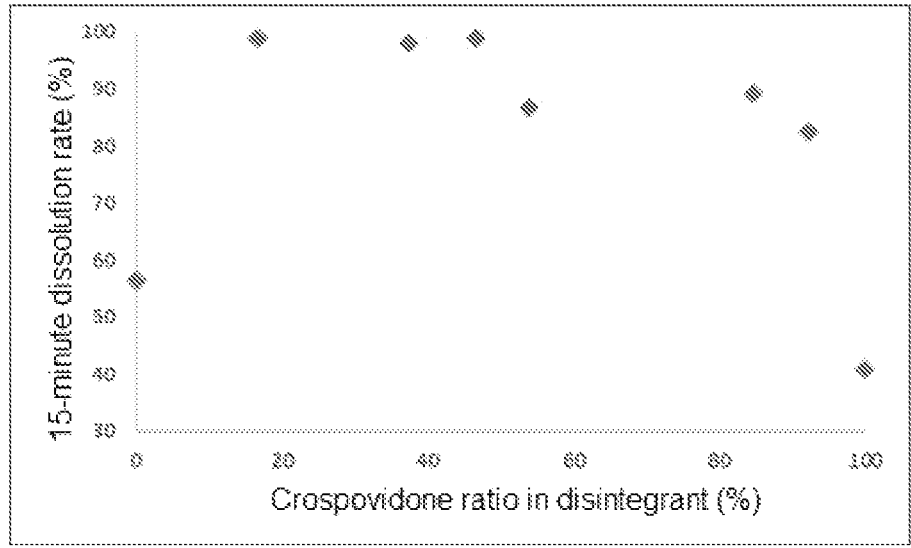

[Figure 3]
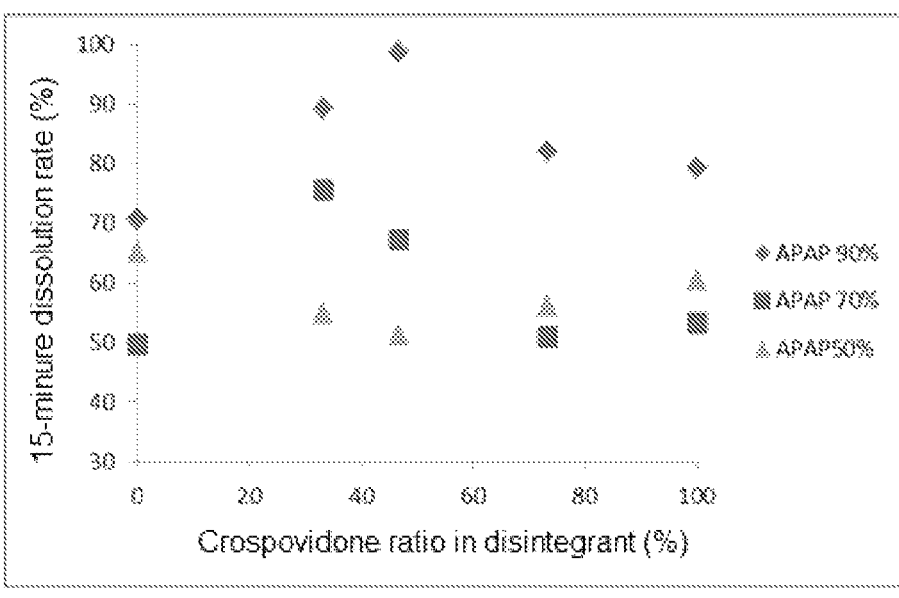

TABLET AND METHOD FOR MANUFACTURING SAME

TECHNICAL FIELD

Cross-Reference to Related Applications

The present application claims convention priority based on Japanese Patent Application No. 2020-115271 filed Jul. 3, 2020 and Japanese Patent Application No. 2021-000629 filed Jan. 6, 2021, which are incorporated herein by reference in their entirety.

The present invention relates to a tablet, or a pharmaceutical composition, that contains acetaminophen at a high concentration. The present invention further relates to a method for manufacturing this tablet.

BACKGROUND ART

Acetaminophen is an antipyretic analgesic with few side effects and, as a result, is frequently used by patients in a broad range of ages. When used medically for pain relief, e.g., headaches, lower back pain, and so forth, the dose and route of administration for acetaminophen, considered as acetaminophen in adults, is the oral administration of 300 to 1000 mg per dose at a dosage interval of at least 4 to 6 hours, with a limit of a total of 4,000 mg in one day. At present, acetaminophen tablets on the market include 500 mg tablets, 300 mg tablets, and 200 mg tablets in terms of the amount of active ingredient.

Fluidized bed granulation, which is a wet granulation method, is currently the most widely used method of drug production (PTL 1 and PTL 2). In the fluidized bed granulation method, generally the drug and additives are introduced into a fluidized bed granulator and are fluidized and a binder solution, or a binder solution in which the drug is dissolved or suspended, is added by spraying. Using this method, granules adapted for tableting are obtained with drug particles that exhibit excellent fluidity, but the particles of a drug lacking excellent fluidity are made finer, and content uniformity may be impaired when there is a difference from the additives in terms of particle size and weight. In this case, it is necessary to add a relatively large amount of the additives in order, inter alia, to improve fluidity and moldability, resulting in larger tablets. In addition, since the fluidized bed granulation method is a method in which the granules, after their preparation by wet granulation, are combined with a lubricant and so forth followed by tableting, this method elicits a large number of manufacturing steps as well as relatively high manufacturing costs.

In contrast to this, the dry direct compression method involves only powder mixing and tableting and thus has fewer steps and lower manufacturing costs. However, the fluidity of the mixed powder is inferior to that in the dry and wet granulation methods, which produce granules, and as a result a large weight variability occurs and problems of compression moldability arises. In particular, the formulation of acetaminophen by dry direct compression has been regarded as problematic because acetaminophen has a complex particle shape and also exhibits very strong secondary cohesive forces, caused by, for example, intermolecular forces (van der Waals forces) and electrostatic charging, and is a powder with a very poor fluidity.

PTL 3 is an example of a method for manufacturing acetaminophen tablets by dry direct compression. PTL 3 discloses the use of unmilled acetaminophen for tablet manufacture, the method including a step in which a dispersing agent, lubricant, and other additives are blended into an unmilled acetaminophen, and a step, which is carried out at least once prior to additive blending or after the blending of each additive, and in which deagglomeration and particle size adjustment are carried out to bring about the dispersion or attachment of the additive on or to the surface of the acetaminophen particle.

CITATION LIST

Patent Literature

[PTL 1] Japanese Patent Application Laid-open No. 2013-216610

[PTL 2] Japanese Translation of PCT Application No. 2015-63521

[PTL 3] Japanese Patent Application Laid-open No. 2018-90638

The descriptions in PTL 1 to PTL 3 are incorporated herein by reference in their entirety.

SUMMARY OF INVENTION

Technical Problem

PTL 3 describes a moisture adjustment step, i.e., the addition of water by spraying to implement mixing, and it is considered that this moisture adjustment is performed in order to raise the tablet hardness. PTL 3 also describes a method including a step, which is carried out at least once prior to additive blending or after the blending of each additive, and in which deagglomeration and particle size adjustment are carried out to bring about the dispersion or attachment of the additive on or to the surface of the acetaminophen particle. The number of steps is thus larger than in the most convenient dry direct compression method, i.e., mixing additives with the active pharmaceutical ingredient and tableting. Thus, the problem to be addressed is the development of an acetaminophen tablet that can be manufactured by an even more convenient dry direct compression method.

In addition, since the cost of acetaminophen is very low, many of the additives blended therewith are more expensive. The incorporation of acetaminophen at high concentrations in order to reduce the amount of additive incorporation is thus crucial for reducing manufacturing costs. The incorporation of acetaminophen at high concentrations is also required from the standpoint of dosing compliance and adherence. Moreover, a standard of an dissolution rate of at least 80% in 15 minutes, pursuant to the official dissolution test standard in Part 3 of the Japanese Pharmaceutical Codex, has been established for acetaminophen tablets, and this dissolution standard must be satisfied.

Thus, the problem to be solved by the present invention is: to provide a tablet that contains a high concentration of acetaminophen, that exhibits a rate of acetaminophen dissolution from the tablet at least 80% in 15 minutes, and that can be manufactured by dry direct compression; and to provide a manufacturing method therefor.

Solution to Problem

As a result of intensive investigations in view of this problem, the present inventors discovered that a tablet that contains a high acetaminophen concentration and that satisfies the dissolution test standard, is obtained by manufacturing by mixing an acetaminophen active pharmaceutical ingredient having a prescribed particle diameter range with a prescribed crystalline cellulose and at least two types of disintegrants and carrying out direct compression tableting. The present invention was achieved on the basis of this knowledge.

That is, the following inventions are provided by the present invention.

[1] A tablet including: acetaminophen that has a median particle diameter in a range from 100 to 350 µm; crystalline cellulose that has a bulk density in a range from 0.10 to 0.23 g/cm³; and at least two types of disintegrants, wherein the at least two types of disintegrants are (a) at least one disintegrant selected from the group consisting of crospovidone, croscarmellose sodium, and sodium starch glycolate, and (b) a disintegrant that is a low-substituted hydroxypropyl cellulose, and wherein the acetaminophen content per tablet is at least 86 weight %.

[2] The tablet according to [1], wherein the tablet hardness is at least 50 N.

[3] The tablet according to [1] or [2], wherein the crystalline cellulose content in each tablet is at least 7.3 weight %.

[4] The tablet according to any one of [1] to [3], wherein a ratio of the disintegrant (a) in the at least two types of disintegrants incorporated in each tablet is 15 to 95 weight %.

[5] The tablet according to any one of [1] to [4], wherein a total content of the disintegrants (a) and (b) in each tablet is 1.0 to 4.0 weight %.

[6] The tablet according to any one of [1] to [5], wherein an acetaminophen dissolution rate is at least 80% in 15 minutes.

[7] A method for manufacturing the tablet according to any one of [1] to [6], the method including: a step of obtaining a powder mixture by mixing acetaminophen that has a median particle diameter in a range from 100 to 350 µm, crystalline cellulose that has a bulk density in a range from 0.10 to 0.23 g/cm³, and at least two types of disintegrants; and a step of obtaining a tablet by direct compression tableting of the powder mixture, wherein the at least two types of disintegrants are (a) at least one disintegrant selected from the group consisting of crospovidone, croscarmellose sodium, and sodium starch glycolate, and (b) a disintegrant that is a low-substituted hydroxypropyl cellulose.

[8] A pharmaceutical composition including: acetaminophen that has a median particle diameter in a range from 100 to 350 µm; crystalline cellulose that has a bulk density in a range from 0.10 to 0.23 g/cm³; and at least two types of disintegrants, wherein the at least two types of disintegrants are (a) at least one disintegrant selected from the group consisting of crospovidone, croscarmellose sodium, and sodium starch glycolate, and (b) a disintegrant that is a low-substituted hydroxypropyl cellulose, and wherein the acetaminophen content in each unit of administration is at least 86 weight %.

[9] The pharmaceutical composition according to [8], wherein the pharmaceutical composition is a tablet for oral administration and the tablet hardness is at least 50 N.

[10] The pharmaceutical composition according to [8] or [9], wherein a crystalline cellulose content in each unit of administration is at least 7.3 weight %.

[11] The pharmaceutical composition according to any one of [8] to [10], wherein a ratio of the disintegrant (a) in the at least two types of disintegrants incorporated in each unit of administration is 15 to 95 weight %.

[12] The pharmaceutical composition according to any one of [8] to [11], wherein a total content of the disintegrants (a) and (b) in each unit of administration is 1.0 to 4.0 weight %.

4

[13] The pharmaceutical composition according to any one of [8] to [12], wherein an acetaminophen dissolution rate is at least 80% in 15 minutes.

Advantageous Effects of Invention

The present invention can thus provide a tablet that contains a high concentration of acetaminophen and that exhibits an acetaminophen dissolution rate that satisfies at least 80% in 15 minutes. The present invention can also provide a tablet manufacturing method that uses dry direct compression, is convenient, and has a low manufacturing cost.

BRIEF DESCRIPTION OF DRAWINGS

FIG. 1 is an dissolution curve for the tablet A1 and the tablet B manufactured in Example 1. The vertical axis is the acetaminophen dissolution rate, and the horizontal axis is the test solution collection time (min).

FIG. 2 is a graph that shows the relationship between the ratio of crospovidone in the two types of disintegrants and the 15-minute dissolution rate (%).

FIG. 3 is a graph that shows the relationship among the ratio of crospovidone in the two types of disintegrants, the acetaminophen (APAP) content, and the 15-minute dissolution rate (%).

DESCRIPTION OF EMBODIMENTS

Embodiments for carrying out the present invention are particularly described in the following. Numerical value ranges that are indicated using "to" in the present Description denote ranges that include the numerical values indicated before and after the "to" as the lower and upper limits.

(Tablet)

The present invention relates to a tablet including: acetaminophen that has a median particle diameter in the range from 100 to 350 µm; crystalline cellulose that has a bulk density in the range from 0.10 to 0.23 g/cm³; and at least two types of disintegrants, wherein the at least two types of disintegrants are (a) at least one disintegrant selected from the group consisting of crospovidone, croscarmellose sodium, and sodium starch glycolate, and (b) a disintegrant that is a low-substituted hydroxypropyl cellulose, and the acetaminophen content per tablet is at least 86 weight %.

The physiologically active drug in the tablet according to the present invention is acetaminophen. Acetaminophen is an antipyretic analgesic and is used to treat symptoms such as fever, chills, headache, and so forth. The tablet and pharmaceutical composition according to the present invention contain acetaminophen in a pharmaceutically effective amount and can be administered orally to the patient who requires treatment with same. The tablet manufacturing method according to the present invention is described below.

The tablet according to the present invention may be a conventional tablet or may be an orally disintegrating tablet, but is preferably a conventional tablet. In addition, the tablet according to the present invention may be an uncoated tablet provided by compression molding by, for example, tableting (compression-molded tablet), or may be a coated tablet provided with a coating layer on the periphery of an uncoated tablet, but is preferably an uncoated tablet.

The median particle diameter (D50) of the acetaminophen active pharmaceutical ingredient used in the tablet according to the present invention (referred to hereinbelow as the present acetaminophen active pharmaceutical ingredient) is in the range of 100 to 350 μm and is preferably in the range of 120 to 330 μm. With regard to the particle size distribution exhibited by the present acetaminophen active pharmaceutical ingredient, D10 is in the range from 5 to 200 μm, preferably in the range from 10 to 170 μm, and more preferably in the range from 20 to 150 μm, and D90 is in the range from 200 to 600 μm, preferably in the range from 250 to 550 μm, and more preferably in the range from 250 to 530 μm.

There may be some differences between manufacturing lots. In addition, the volume-average particle diameter (MV) of the present acetaminophen active pharmaceutical ingredient can be in the range from 100 to 350 μm and may be in the range from 120 to 330 μm. There may be some differences between manufacturing lots. The particle size distribution in the present invention is acquired by evaluation of the volumetric distribution using dry particle diameter measurement by a laser diffraction method (Laser Micron Sizer LMS-2000e (Seishin Enterprise Co., Ltd.)). D50 is the particle diameter at the 50% accumulation of the individual volumes from the small diameter side of the particle size distribution, and is referred to as the median particle diameter.

The present acetaminophen active pharmaceutical ingredient used may be one that has not been subjected to special treatment post-crystallization or may be one that has been subjected to a sieving treatment post-crystallization. In an embodiment of the present invention, a present acetaminophen active pharmaceutical ingredient can be used that has not been subjected to a milling treatment post-crystallization. In a preferred embodiment of the present invention, the present acetaminophen active pharmaceutical ingredient is subjected to a sieving treatment post-crystallization. A sieving treatment functions to provide a powder that contains larger amounts of particles with particle diameters adapted to the production of the tablet according to the present invention. It is thought that, due to a poor disintegratability, a viable tablet is not obtained when an active pharmaceutical ingredient is used that contains large amounts of coarse acetaminophen crystals (for example, a D50 of at least 400 μm). It is also thought that compression tablet molding will be problematic in the case of tablets provided by tableting using an active pharmaceutical ingredient that contains large amounts of acetaminophen fines (for example, less than or equal to 30 μm). A sieving treatment can remove the coarse acetaminophen crystals and the acetaminophen fines.

The acetaminophen content in the tablet according to the present invention is at least 86 weight %. This is because the tablet will not become excessively large, even when 200 to 500 mg of acetaminophen is present in each tablet, when the acetaminophen content is at least 86 weight %. As a tablet assumes a larger size, the tablet becomes more difficult to swallow and the ease of intake is reduced. The acetaminophen content in each tablet may be in the range from 86 to 95 weight %, or in the range from 86 to 94 weight %, or in the range from 86 to 93 weight %, or in the range from 86 to 92 weight %, or in the range from 86 to 91 weight %, or in the range from 86 to 90 weight %. In the present Description, a statement that acetaminophen is incorporated at a high concentration indicates a high acetaminophen content in each tablet or per tablet (for example, a content of at least 86 weight %).

In a particular embodiment of the present invention, the acetaminophen content in the tablet may be at least 90 weight %. A content of at least 90 weight % may be particularly preferred when a tablet having an acetaminophen content of 500 mg per tablet is manufactured.

The tablet according to the present invention may contain at least 200 mg of acetaminophen per tablet. As a general matter, adults often take 300 to 500 mg as acetaminophen per os in a single administration, and thus, when the content per tablet is at least 200 mg, one or two tablets may be taken for a single administration, which is practical. The tablet according to the present invention may have an acetaminophen content per tablet of at least 300 mg.

The tablet according to the present invention contains crystalline cellulose having a bulk density in the range from 0.10 to 0.23 g/cm³. This bulk density can be measured in accordance with the bulk density measurement method described in "The Japanese Pharmacopoeia 17th Edition, 3. Powder Property Determinations, 3.01 Determination of Bulk and Tapped Densities". There are numerous types of crystalline cellulose, and generally different types are used in correspondence to the particular application, e.g., disintegrant, filler, binder, and so forth. Crystalline cellulose having a bulk density in the range of 0.10 to 0.23 g/cm³ can be used in the present invention in order to raise the tablet moldability. It can be said that crystalline cellulose having a bulk density in the range of 0.10 to 0.23 g/cm³ exhibits a high moldability. Crystalline cellulose having a bulk density in the range of 0.10 to 0.23 g/cm³ is also referred to in the present Description as high-moldability crystalline cellulose. The high-moldability crystalline cellulose used in the present invention may have an average particle diameter in the range from 20 to 100 μm. In addition, the high-moldability crystalline cellulose used in the present invention may have a high aspect ratio. This is because entanglement readily occurs due to the long, thin shape and the moldability is excellent. High-moldability crystalline cellulose products having such an average particle diameter and bulk density can be exemplified by Ceolus (registered trademark) OD20-P and KG-1000 (Asahi Kasei Corporation), but are not limited to these. The use of crystalline cellulose having a bulk density in the range of 0.10 to 0.15 g/cm³ is preferred in an embodiment of the present invention. A crystalline cellulose product having the preferred bulk density can be exemplified by Ceolus (registered trademark) KG-1000 (Asahi Kasei Corporation), but there is no limitation to this.

The tablet according to the present invention can contain at least 7.3 weight % high-moldability crystalline cellulose per tablet. By having the content of high-moldability crystalline cellulose per tablet be at least 7.3 weight %, a tablet can be manufactured that exhibits a tablet hardness satisfactorily resistant to the impact that may be received during the manufacturing and distribution steps. The content of high-moldability crystalline cellulose per tablet can be, besides at least 7.3 weight %, for example, at least 7.4 weight %, or at least 7.5 weight %, or at least 7.6 weight %, or at least 7.7 weight %, or at least 7.8 weight %, or at least 7.9 weight %, or at least 8.0 weight %. Even when the acetaminophen is incorporated at high concentrations (for example, 86 weight %), the incorporation of at least 7.3 weight % high-moldability crystalline cellulose makes it possible to manufacture a tablet that has a hardness of at least 50 N.

The upper limit on the content per tablet of high-moldability crystalline cellulose is approximately 12 weight %. This is because, due to the incorporation of the acetaminophen at high concentrations of at least 86 weight %, there are limitations on the contents of the other components in the tablet according to the present invention. The content of high-moldability crystalline cellulose per tablet, besides not more than 12 weight %, can be, for example, not more than 11.9 weight %, or not more than 11.8 weight %, or not more than 11.7 weight %, or not more than 11.6 weight %, or not more than 11.5 weight %, or not more than 11.4 weight %, or not more than 11.3 weight %, or not more than 11.2 weight %, or not more than 11.1 weight %, or not more than 11.0 weight %, or not more than 10.9 weight %, or not more than 10.8 weight %. The content of high-moldability crystalline cellulose per tablet can be, for example, in the range from 7.3 weight % to 12.0 weight %, or in the range from 7.3 weight % to 11.9 weight %, or in the range from 7.3 weight % to 11.8 weight %, or in the range from 7.4 weight % to 12.0 weight %, or in the range from 7.4 weight % to 11.9 weight %, or in the range from 7.4 weight % to 11.8 weight %, or in the range from 7.5 weight % to 12.0 weight %, or in the range from 7.5 weight % to 11.9 weight %, or in the range from 7.5 weight % to 11.8 weight %.

The tablet according to the present invention contains at least two types of disintegrants, and the disintegrants can be selected from the group consisting of crospovidone, croscarmellose sodium, sodium starch glycolate, croscarmellose, sodium carboxymethyl starch, gelatin, starch, corn starch, low-substituted hydroxypropyl cellulose, and potato starch.

In a preferred embodiment of the present invention, the tablet contains at least two types of disintegrants and the at least two types of disintegrants are (a) at least one disintegrant selected from the group consisting of crospovidone, croscarmellose sodium, and sodium starch glycolate, and (b) a disintegrant that is a low-substituted hydroxypropyl cellulose.

The content of the disintegrants (a) and (b) in the tablet according to the present invention can be altered as appropriate depending on the contents of the acetaminophen active pharmaceutical ingredient, crystalline cellulose, and lubricant. The tablet according to the present invention can contain a total amount of the disintegrants (a) and (b) of, for example, not more than 4.0 weight %, or not more than 3.9 weight %, or not more than 3.8 weight %, or not more than 3.7 weight %, or not more than 3.6 weight %, or not more than 3.5 weight %, or not more than 3.4 weight %, or not more than 3.3 weight %, or not more than 3.2 weight %, or not more than 3.1 weight %, or not more than 3.0 weight %, or not more than 2.9 weight %, or not more than 2.8 weight %, or not more than 2.7 weight %, or not more than 2.6 weight %, or not more than 2.5 weight %, or not more than 2.4 weight %, or not more than 2.3 weight %, or not more than 2.2 weight %, or not more than 2.1 weight %, or not more than 2.0 weight %, and of at least 1.0 weight %, or at least 1.1 weight %, or at least 1.2 weight %, or at least 1.3 weight %, or at least 1.4 weight %, or at least 1.5 weight %. The range for the total content of the disintegrants (a) and (b) can be, for example, the range of 1.0 to 4.0 weight % for the total amount, or the range of 1.0 to 3.5 weight % for the total amount, or the range of 1.0 to 3.0 weight % for the total amount, but there is no limitation to these. The total content of the disintegrants (a) and (b) can be varied as appropriate, in particular depending on the content of the acetaminophen active pharmaceutical ingredient and the content of the crystalline cellulose, so as to satisfy the dissolution standard of an dissolution rate of at least 80% in 15 minutes and/or so as to enhance the storage stability. Measurement in the dissolution test can be carried out on the basis of the dissolution test procedure described in The Japanese Pharmacopoeia 17th Edition. The 15-minute dissolution rate is the dissolution rate from the start of the test to the elapse of 15 minutes. More specifically, the measurement can be carried out on the basis of the second method (paddle method) under the dissolution test procedures under General Test Methods of The Japanese Pharmacopoeia.

The present inventors have surprisingly discovered that the dissolution standard of a 15-minute dissolution rate of at least 80% is satisfied by the incorporation of a combination of at least two types rather than just one type, i.e., either disintegrant (a) or disintegrant (b). Specifically, and as shown in the examples, the dissolution standard of a 15-minute dissolution rate of at least 80% can be satisfied by the incorporation of a combination of (a) at least one disintegrant selected from the group consisting of crospovidone, croscarmellose sodium, and sodium starch glycolate, with (b) a disintegrant that is a low-substituted hydroxypropyl cellulose. The rapid expression of the antipyretic analgesic effect of acetaminophen can be expected when the dissolution standard of a 15-minute dissolution rate of at least 80% is satisfied. It was found, on the other hand, that the dissolution standard of a 15-minute dissolution rate of at least 80% is not satisfied by a tablet containing only crospovidone or by a tablet containing only low-substituted hydroxypropyl cellulose.

The tablet according to the present invention can contain the at least two types of disintegrants (a) and (b) at a prescribed ratio. The ratio of the disintegrant (a) in the total of the disintegrants (a) and (b) incorporated in each tablet according to the present invention may be 15 to 95 weight %, preferably 20 to 90 weight %, more preferably 20 to 80 weight %, and still more preferably 30 to 80 weight %.

The tablet according to the present invention may additionally contain a dispersing agent. The dispersing agent is preferably hydrated silicon dioxide or light anhydrous silicic acid. The percentage of incorporation for the dispersing agent may be 0.1 to 2 weight % with reference to 100 weight % for the formulation.

The tablet according to the present invention may additionally contain a lubricant. The lubricant is preferably magnesium stearate. The percentage of incorporation for the lubricant may be 0.1 to 2 weight % with reference to 100 weight % for the formulation.

With regard to tablet hardness, it is thought that a tablet having a hardness of at least 50 N generally can withstand, for example, the impact when the tablet is packaged, e.g., in PTP, the impact during transport, and the force from handling by the patient. The tablet according to the present invention has a tablet hardness of at least 50 N, and the tablet hardness may be at least 51 N, or at least 52 N, or at least 53 N, or at least 54 N, or at least 55 N, or at least 56 N, or at least 57 N, or at least 58 N, or at least 59 N, or at least 60 N. There are no particular limitations on the upper limit for the tablet hardness in the present invention, but this may be not more than 150 N or not more than 100 N. The tablet hardness can be measured using, for example, a load cell-type tablet hardness analyzer (PC-10, Okada Seiko Co., Ltd.).

The acetaminophen dissolution rate of the tablet according to the present invention can be at least 80% in 15 minutes, and the acetaminophen dissolution rate is preferably at least 85% in 15 minutes and more preferably the acetaminophen dissolution rate is at least 90% in 15 minutes.

The tablet according to the present invention can further contain additives (referred to as other additives in the following) other than the aforementioned high-moldability crystalline cellulose, disintegrants, dispersing agent, and lubricant. These other additives can be exemplified by fillers such as D-mannitol and lactose; fluidizers such as anhydrous silicon dioxide, calcium silicate, silicic acid dihydrate, and magnesium aluminometasilicate; stabilizers such as cyclodextrin; colorants; and so forth; however, there is no limitation to these and the usual additives used in the production of drug and pharmaceutical products can be used. When a fluidizer is incorporated, it can be incorporated in the range of 0.1 to 1.0 weight % per tablet.

With regard to the size of the tablet according to the present invention, it can have a diameter in the range of 6 mm to 18 mm, an aspect ratio in the range of 1 to 3, and a thickness in the range of 2 mm to 10 mm, but there is no limitation to these ranges. With regard to shape, the tablet according to the present invention may be a standard or conventional tablet or may be an irregularly shaped tablet, and may have, for example, a circular, oval, or caplet shape; however, there is no limitation to these.

(Tablet Manufacturing Method)

Another aspect of the present invention relates to a method for manufacturing the hereinabove-described tablet, the method including: a step of obtaining a powder mixture by mixing acetaminophen that has a median particle diameter in the range from 100 to 350 μm, crystalline cellulose that has a bulk density in the range from 0.10 to 0.23 g/cm³, and at least two types of disintegrants; and a step of obtaining a tablet by direct compression tableting of the powder mixture, wherein the at least two types of disintegrants are (a) at least one disintegrant selected from the group consisting of crospovidone, croscarmellose sodium, and sodium starch glycolate, and (b) a disintegrant that is a low-substituted hydroxypropyl cellulose.

The "step of obtaining a powder mixture by mixing acetaminophen that has a median particle diameter in the range from 100 to 350 μm, crystalline cellulose that has a bulk density in the range from 0.10 to 0.23 g/cm³, and at least two types of disintegrants" (referred to in the following as the mixing step) in the manufacturing method according to the present invention is a step in which the acetaminophen that is the physiologically active drug in the tablet, is mixed with the other components prior to tableting to give the tablet. These other components are the other additives in addition to the high-moldability crystalline cellulose and the disintegrants.

With regard to the acetaminophen having a median particle diameter in the range from 100 to 350 μm, the high-moldability crystalline cellulose, the disintegrants, and the other additives, the same ones as described under the previous (Tablet) section can be used.

In the present Description, "mixing" indicates the mixing of two or more species of powders. The terms used in this field include "milling", but this denotes the grinding or break-up of particles to obtain smaller particles. On the other hand, in the present Description "mixing" is a process that lacks an action that brings about a finer particle diameter for the powder. In addition, the "deagglomeration and particle size adjustment" used in this field denotes a breaking up of agglomerated or aggregated particles. While a strong "shear force" is applied to the powder in milling and in deagglomeration and particle size adjustment, mixing is a process in which the "shear force" is weak. For example, in the case of a powder in which fines region acetaminophen particles are substantially aggregated, a strong "shear force" is required in order to break out the individual particles, and this process is a deagglomeration and particle size adjustment. Moreover, milling is the process of breaking up particles using a strong "shear force".

The mixing step in the present manufacturing method can be carried out using, for example, a V-mixer, container mixer, and so forth. A V-mixer is a device that carries out a rapid and uniform mixing by rotating a V-shaped mixing container and moving the powder or particles in the container on the whole to impart a convective motion. The use of a V-mixer generally enables the execution of a gentle mixing without the application of excessive force to the powder or particles. The mixing conditions can be varied as appropriate depending on the scale, but, for example, mixing can be performed at a rotation rate of 5 to 50 rpm for about 1 to 15 minutes.

The mixing step in the present manufacturing method may be implemented as a one-time mixing operation or may be implemented divided into two or more mixing operations. When carried out as a one-time mixing operation, all of the components contained in the tablet are introduced into, for example, a V-mixer, and mixing is carried out. When carried out divided into two or more mixing operations, the components contained in the tablet can be divided into the two or more times according to the species and can be introduced into the V-mixer and mixing can be carried out. For example, in a first mixing, the components other than the lubricant (for example, magnesium stearate) and dispersing agent (for example, hydrated silicon dioxide or light anhydrous silicic acid) can be introduced into, for example, a V-mixer, and mixing can be carried out, and the lubricant and dispersing agent can be added after the first mixing and mixing can be carried out again. Spreading of the lubricant and dispersing agent can be prevented by doing this. The mixing after the addition of the lubricant and dispersing agent can be carried out for about 1 to 3 minutes. A powder mixture can be provided by the mixing step of the present manufacturing method. This powder mixture is a particulate aggregation of the components present in the tablet. It is not necessary in the manufacturing method according to the present invention to carry out moisture adjustment, for example, the addition of water.

The "step of obtaining a tablet by direct compression tableting of this powder mixture" (referred to as the tableting step in the following) is a step in which the powder mixture yielded by the mixing step is subjected to direct compression tableting and molding. In the present Description, direct compression tableting denotes tableting by a dry method to obtain a tablet by the direct compression of a powder mixture using a punch and die.

Specifically, tableting can be performed using a tableting machine (e.g., a rotary molding machine). For example, tableting can be carried out by volumetric metering of the powder to be filled into a fixed die cavity, compression molding using upper and lower punches, and finally ejection from the die cavity.

In the manufacturing method according to the present invention, the tableting pressure can be set as appropriate considering, e.g., the tablet hardness, the pressure tolerance of the tableting punches, and so forth, and is in the range of 3 to 50 kN and preferably in the range of 5 to 40 kN. The tableting pressure imparts physical strength, e.g., hardness, to the tablet, and the tablet hardness can decline at a lower tableting pressure. However, when the tableting pressure is increased, the tablet hardness does not necessarily increase in conformity therewith. For example, depending on the components, the tablet hardness may not increase even when the tableting pressure is increased. In addition, when the tableting pressure is high, damage to the tableting punch and tableting problems (capping, sticking) readily occur. It is thus necessary in tableting to apply a pressure in conformity to the properties of the tablet.

Wet methods, e.g., fluidized bed granulation, are commonly used tablet manufacturing methods. However, wet granulation has a large number of steps and relatively high manufacturing costs. The method according to the present invention of the direct compression tableting of a powder can provide a tablet manufacturing method that is simple and convenient and has low manufacturing costs. Moreover, since a water addition step is not used, there is little risk of pollution by, e.g., contamination.

EXAMPLES

The present invention is more particularly described using the following examples, but the present invention is not limited to or by these examples. Unless specifically indicated otherwise, in the present Description "%" is on a weight basis and the numerical value ranges include their endpoints.

Materials and Methods (1) Materials

The following reagents were used in the following examples and comparative examples to manufacture acetaminophen-containing tablets.

Acetaminophen (AA) Active Pharmaceutical Ingredients
  a) acetaminophen S (Yamamoto Corporation Co., Ltd.) (designated below as AA active pharmaceutical ingredient a)
  b) acetaminophen H (Hachidai Pharmaceutical Co., Ltd.) (designated below as AA active pharmaceutical ingredient b)
  c) Dense Powder (SpecGx LLC) (designated below as AA active pharmaceutical ingredient c)
  d) crystals (Granules) (designated below as AA active pharmaceutical ingredient d)
  e) acetaminophen SS (Yamamoto Corporation Co., Ltd.) (designated below as AA active pharmaceutical ingredient e)
  f) acetaminophen J grade (Anqiu Lu'an Pharmaceutical Co., Ltd.) (designated below as AA active pharmaceutical ingredient f)
  g) acetaminophen (Iwaki Seiyaku Co., Ltd.) (designated below as AA active pharmaceutical ingredient g)
crospovidone (CL-F, BASF)
sodium starch glycolate (Primojel, DEF Pharma)
croscarmellose sodium (Kiccolate (registered trademark) ND-200, Asahi Kasei Corporation) low-substituted hydroxypropyl cellulose (LH-11, Shin-Etsu Chemical Co., Ltd.) crystalline cellulose (Ceolus (registered trademark) KG-1000, Asahi Kasei Corporation)
magnesium stearate (Taihei Chemical Industrial Co., Ltd.) hydrated silicon dioxide (Carplex #80, Evonik Japan Co., Ltd.)

(2) Manufacturing Method

The tablet manufacturing method is as follows. First, the AA active pharmaceutical ingredient, crospovidone, low-substituted hydroxypropyl cellulose, and crystalline cellulose were mixed/stirred (42 rpm rotation rate, 10 minute mixing time) using a V-mixer to provide an intermediate tableting powder. The magnesium stearate and hydrated silicon dioxide were added to the intermediate tableting powder and a supplementary mixing/stirring (42 rpm rotation rate, 2 minute mixing time) was carried out to yield a tableting powder. This tableting powder was tableted into tablets using a tableting machine and a punch/die with a diameter of 9 mm.

The following were used: a V-mixer (V-10, Tokuju Seisakusho Co., Ltd.) to mix the tableting powder, a tableting machine (HT-AP15SS-11, Hata Tekkosho Co., Ltd.) for tableting, and plane angle punches/dies. When tableting/molding was possible, tableting was performed with the tableting pressure set to provide a tablet hardness of 50 N or more, taking into consideration, inter alia, the pressure tolerance of the tableting punches.

(3) Measurement of the Particle Diameter of the Acetaminophen Active Pharmaceutical Ingredients The acetaminophen active pharmaceutical ingredients were subjected to dry measurement of the particle diameter by a laser diffraction method. A Laser Micron Sizer LMS-2000e (Seishin Enterprise Co., Ltd.) was used for measurement of the particle size distribution. The measurement was carried out at a dispersion compressed air pressure of 0.5 bar.

(4) Measurement of Tablet Hardness

The tablets manufactured in the following examples were submitted to a hardness measurement test. The hardness measurement was run using a hardness analyzer (PC-30, Okada Seiko Co., Ltd.).

(5) Tablet Dissolution Test

An dissolution test was carried out on the tablets manufactured in the following examples (300 mg acetaminophen content/tablet). The dissolution test was run using a method conforming to the second method (paddle method) under the dissolution test procedures under General Test Methods of The Japanese Pharmacopoeia 17th Edition. Water according to the disintegration test procedures under General Test Methods of The Japanese Pharmacopoeia was used for the test liquid. The dissolution test was run using an dissolution tester (RT-J2000, DS-3, Dainippon Seiki Co., Ltd.) and a spectrophotometer (UV-1000, Shimadzu Corporation).

Specifically, one test tablet was placed in 900 mL of the test liquid being held at a liquid temperature of $37 \pm 0.5°$ C., and, after starting the dissolution test at 50 revolutions per minute, 10 mL of the dissolution liquid was collected at regular time intervals. The sample solution was obtained by filtration across a membrane filter having a pore size of 0.45 μm. 2 mL of the sample solution was introduced into a 100-mL volumetric flask and dilution was performed; 4 mL of the dilution was introduced into a 100-mL volumetric flask and dilution was performed; and measurement with the spectrophotometer (measurement wavelength: 243 nm) was performed and the dissolution rate was calculated. The dissolution standard was determined to be satisfied when the 15-minute dissolution rate was 80% or more.

Example 1: Examination of the Particle Diameter and Dissolution Rate of Acetaminophen (AA) Active Pharmaceutical Ingredients The particle diameter measurement results for the seven AA active pharmaceutical ingredients are given in Table 1.

TABLE 1

|  | AA API a | AA API b | AA API c | AA API d | AA API e | AA API f | AA API g |
|---|---|---|---|---|---|---|---|
| MV (μm) | 234 | 202 | 173 | 452 | 46 | 222 | 306 |
| D10 (μm) | 73 | 62 | 27 | 75 | 5.7 | 42 | 125 |

13        14

TABLE 1-continued

|  | AA API a | AA API b | AA API c | AA API d | AA API e | AA API f | AA API g |
|---|---|---|---|---|---|---|---|
| D50 (μm) | 224 | 191 | 147 | 419 | 26 | 202 | 288 |
| D90 (μm) | 404 | 353 | 357 | 855 | 116 | 426 | 516 |

API: active pharmaceutical ingredient

Tablets were then manufactured using the five AA active pharmaceutical ingredients designated active pharmaceutical ingredients a to e and using the compositions and conditions given in Table 2. The dissolution test was performed on each of the tablets. When AA active pharmaceutical ingredient e was used, even with the application of the maximum force by the tableting machine, it was not possible to manufacture a tablet containing 300 mg (90%) of the AA active pharmaceutical ingredient and having a tablet weight of 333 mg. This is thought to be due to the high bulkiness of the AA active pharmaceutical ingredient e.

ever, they were demonstrated to have equivalent dissolution characteristics. It is thought that an optimal adjustment of the dissolution characteristics can be made by varying the blending ratios for the disintegrants and the crystalline cellulose. The tablets A1 and B were tableted at a tableting pressure of 20 kN in both instances.

Example 2: Examination of the Dissolution Rate and Amount of Disintegrant Addition The dissolution rate and the amounts of addition of the two disintegrants were examined. Tablets A4 to A8 were manufactured using the AA active pharmaceutical ingredient a and the compositions given in Table 3. The blending ratios of the crospovidone and low-substituted hydroxypropyl cellulose disintegrants were varied in tablets A4 to A8. Tablets A4 to A8 contained 90% acetaminophen, but could be direct compression tableted. The tablets were also submitted to dissolution testing.

TABLE 2

|  |  | tablet A1 | tablet A2 | tablet A3 | tablet B | tablet C | tablet D1 | tablet D2 | tablet E |
|---|---|---|---|---|---|---|---|---|---|
| Composition (%) | AA API a | 90.0 | 90.0 | 90.0 | — | — | — | — | — |
|  | AA API b | — | — | — | 90.0 | — | — | — | — |
|  | AA API c | — | — | — | — | 90.0 | — | — | — |
|  | AA API d | — | — | — | — | — | 90.0 | 90.0 | — |
|  | AA API e | — | — | — | — | — | — | — | 90.0 |
| Disintegrant | Crospovidone | 0.5 | 0.7 | 1.1 | 0.3 | 0.7 | 0 | 0.7 | 0.7 |
|  | Low-substituted hydroxypropyl cellulose | 0.9 | 0.8 | 0.4 | 1.5 | 0.8 | 1.5 | 0.8 | 0.8 |
|  | Crystalline cellulose | 7.9 | 7.8 | 7.8 | 7.5 | 7.8 | 7.8 | 7.8 | 7.8 |
|  | Magnesium stearate | 0.2 | 0.2 | 0.2 | 0.2 | 0.2 | 0.2 | 0.2 | 0.2 |
|  | Hydrated silicon dioxide | 0.5 | 0.5 | 0.5 | 0.5 | 0.5 | 0.5 | 0.5 | 0.5 |
|  | Crospovidone ratio in disintegrant (%) | 35.7 | 46.7 | 73.3 | 16.7 | 46.7 | 0.0 | 46.7 | 46.7 |
|  | Total | 100.0 | 100.0 | 100.0 | 100.0 | 100.0 | 100.0 | 100.0 | 100.0 |
| Characteristics | AA content (mg) | 300.0 | 300.0 | 300.0 | 300.0 | 300.0 | 300.0 | 300.0 |  |
|  | Diameter of tablet (mm) | 9 | 9 | 9 | 9 | 9 | 9 | 9 |  |
|  | Thickness of tablet (mm) | 4.5 | 4.5 | 4.5 | 4.5 | 4.5 | 4.5 | 4.5 |  |
|  | Weight of tablet (mg) | 333 | 333 | 333 | 333 | 333 | 333 | 333 |  |
|  | Tablet hardness (N) | 73 | 60 | 73 | 74 | 59 | 75 | 60 |  |
|  | 15-minute dissolution rate (%) | 98 | 99 | 82 | 99 | 91 | 66 | 76 |  |

API: active pharmaceutical ingredient

The dissolution standard (15-minute dissolution rate of at least 80%) was satisfied by the tablets A1, A2, and A3 manufactured using the AA active pharmaceutical ingredient a, the tablet B manufactured using the AA active pharmaceutical ingredient b, and the tablet C manufactured using the AA active pharmaceutical ingredient c. On the other hand, the dissolution standard was not satisfied by the tablets D1 and D2 manufactured using the AA active pharmaceutical ingredient d. This example demonstrated that the average particle diameter of the AA active pharmaceutical ingredient used in tablet manufacture affects the tablet dissolution rate and the acetaminophen content. Tablets satisfying the dissolution standard could be manufactured in Example 7, infra, using the active pharmaceutical ingredients f and g. Thus, the range of the average particle diameter of the AA active pharmaceutical ingredient that is suitable for manufacturing the tablet according to the present invention is considered to the range of 100 to 350 μm for the median particle diameter.

FIG. 1 shows the dissolution curve for the tablets A1 and B described in Table 2. Tablets A1 and B have different AA active pharmaceutical ingredients and different blending ratios for the disintegrants and crystalline cellulose; how-

TABLE 3

| Tablet name |  | tablet A4 | tablet A5 | tablet A6 | tablet A7 | tablet A8 |
|---|---|---|---|---|---|---|
| Composition (%) | AA API a | 90.0 | 90.0 | 90.0 | 90.0 | 90.0 |
|  | Disintegrant Crospovidone | 0.0 | 0.7 | 1.1 | 1.2 | 1.3 |
|  | Low-substituted hydroxypropyl cellulose | 1.3 | 0.6 | 0.2 | 0.1 | 0.0 |
|  | Crystalline cellulose | 8.0 | 8.0 | 8.0 | 8.0 | 8.0 |
|  | Magnesium stearate | 0.2 | 0.2 | 0.2 | 0.2 | 0.2 |
|  | Hydrated silicon dioxide | 0.5 | 0.5 | 0.5 | 0.5 | 0.5 |
|  | Total | 100.0 | 100.0 | 100.0 | 100.0 | 100.0 |
|  | Crospovidone ratio in disintegrant (%) | 0.0 | 53.8 | 84.6 | 92.3 | 100.0 |
| Characteristics | AA content (mg) | 300 | 300 | 300 | 300 | 300 |
|  | Diameter of tablet (mm) | 9 | 9 | 9 | 9 | 9 |
|  | Thickness of tablet (mm) | 4.5 | 4.5 | 4.5 | 4.5 | 4.5 |
|  | Weight of tablet (mg) | 333 | 333 | 333 | 333 | 333 |
|  | Tablet hardness (N) | 61 | 72 | 61 | 60 | 59 |
|  | 15-minute dissolution rate (%) | 56 | 87 | 89 | 83 | 41 |

API: active pharmaceutical ingredient 15                                              16

Tablet A4 contained only low-substituted hydroxypropyl cellulose as its disintegrant and had a 15-minute dissolution rate of 56% and did not satisfy the dissolution standard. Tablet A8 contained only crospovidone as its disintegrant and had a 15-minute dissolution rate of 41% and did not satisfy the dissolution standard.

Tablet A5 contained approximately 53.8% crospovidone in the disintegrant and had a 15-minute dissolution rate of 87% and satisfied the dissolution standard. Tablet A6 contained approximately 84.6% crospovidone in the disintegrant and had a 15-minute dissolution rate of 89% and satisfied the dissolution standard. Tablet A7 contained approximately 92.3% crospovidone in the disintegrant and had a 15-minute dissolution rate of 83% and satisfied the dissolution standard. In addition, the tablet A1 in Example 1 contained approximately 35.7% crospovidone in the disintegrant and had a 15-minute dissolution rate of 98% and satisfied the dissolution standard. The tablet A2 in Example 1 contained approximately 46.7% crospovidone in the disintegrant and had a 15-minute dissolution rate of 99% and satisfied the dissolution standard. The tablet A3 in Example 1 contained approximately 73.3% crospovidone in the disintegrant and had a 15-minute dissolution rate of 82% and satisfied the dissolution standard. The tablet B in Example 1 contained approximately 16.7% crospovidone in the disintegrant and had a 15-minute dissolution rate of 99% and satisfied the dissolution standard.

A graph of the crospovidone ratio in the disintegrant and the 15-minute dissolution rate is given in FIG. 2. It was confirmed that the 15-minute dissolution rate was changed by changes in the blending ratio between the crospovidone and low-substituted hydroxypropyl cellulose.

Example 3: Examination of the Acetaminophen Content

Tablets were manufactured using AA active pharmaceutical ingredient a and the compositions given in Table 4. The blending ratios for the acetaminophen and the crospovidone and low-substituted hydroxypropyl cellulose disintegrants were varied in the tablets A90-1 to A90-5, A70-1 to A70-5, and A50-1 to A50-5 indicated in Table 4. All of the tablets indicated in Table 4 could be direct compression tableted. Dissolution testing was also run on the tablets.

The compositions and properties of the tablets are given in Table 4.

As shown in FIG. 3, the dissolution rate varied with the blending ratio for the active pharmaceutical ingredient and the blending ratio for the disintegrant.

Example 4: Second Examination of the Acetaminophen Content

Tablets were manufactured using AA active pharmaceutical ingredient a and the compositions in Table 5. All of the tablets indicated in Table 5 could be direct compression tableted. Dissolution testing was also run on the tablets. The compositions and properties of the tablets are given in Table 5.

TABLE 5

| Tablet name | | A80 | A85 | A86 | A87 | A88 | A89 |
|---|---|---|---|---|---|---|---|
| AA API a | | 80.0 | 85.0 | 86.0 | 87.0 | 88.0 | 89.0 |
| Disintegrant | Crospovidone | 0.7 | 0.7 | 0.7 | 0.7 | 0.7 | 0.7 |
| | Low-substituted hydroxypropyl cellulose | 0.8 | 0.8 | 0.8 | 0.8 | 0.8 | 0.8 |
| Crystalline cellulose | | 17.8 | 12.8 | 11.8 | 10.8 | 9.8 | 8.8 |
| Magnesium stearate | | 0.2 | 0.2 | 0.2 | 0.2 | 0.2 | 0.2 |
| Hydrated silicon dioxide | | 0.5 | 0.5 | 0.5 | 0.5 | 0.5 | 0.5 |
| Total | | 100.0 | 100.0 | 100.0 | 100.0 | 100.0 | 100.0 |
| Crospovidone ratio in disintegrant (%) | | 46.7 | 46.7 | 46.7 | 46.7 | 46.7 | 46.7 |
| AA content (mg) | | 300.0 | 300.0 | 300.0 | 300.0 | 300.0 | 300.0 |
| Diameter of tablet (mm) | | 9 | 9 | 9 | 9 | 9 | 9 |
| Thickness of tablet (mm) | | 4.5 | 4.5 | 4.5 | 5.4 | 5.4 | 5.4 |
| Weight of tablet (mg) | | 333 | 333 | 333 | 333 | 333 | 333 |
| Tablet hardness (N) | | 64 | 64 | 63 | 59 | 58 | 55 |
| 15-minute dissolution rate (%) | | 37 | 48 | 88 | 91 | 95 | 93 |

API: active pharmaceutical ingredient

The acetaminophen blending ratio was varied among the A80, A85, A86, A87, A88, and A89 tablets. The dissolution rate underwent a substantial change between the AA active pharmaceutical ingredient blending ratios of 85% and 86%.

Example 5: Examination of the Disintegrant Type

Tablets were manufactured using the AA active pharmaceutical ingredient a and the compositions given in Table 6.

TABLE 4

| Tablet name | | A90-1 | A90-2 | A90-3 | A90-4 | A90-5 | A70-1 | A70-2 | A70-3 | A70-4 | A70-5 | A50-1 | A50-2 | A50-3 | A50-4 | A50-5 |
|---|---|---|---|---|---|---|---|---|---|---|---|---|---|---|---|---|
| AA API a | | 90.0 | 90.0 | 90.0 | 90.0 | 90.0 | 70.0 | 70.0 | 70.0 | 70.0 | 70.0 | 50.0 | 50.0 | 50.0 | 50.0 | 50.0 |
| Disintegrant | Crospovidone | 0 | 0.5 | 0.7 | 1.1 | 1.5 | 0 | 0.5 | 0.7 | 1.1 | 1.5 | 0 | 0.5 | 0.7 | 1.1 | 1.5 |
| | Low-substituted hydroxypropyl cellulose | 1.5 | 1 | 0.8 | 0.4 | 0 | 1.5 | 1 | 0.8 | 0.4 | 0 | 1.5 | 1 | 0.8 | 0.4 | 0 |
| Crystalline cellulose | | 7.8 | 7.8 | 7.8 | 7.8 | 7.8 | 27.8 | 27.8 | 27.8 | 27.8 | 27.8 | 47.8 | 47.8 | 47.8 | 47.8 | 47.8 |
| Magnesium stearate | | 0.2 | 0.2 | 0.2 | 0.2 | 0.2 | 0.2 | 0.2 | 0.2 | 0.2 | 0.2 | 0.2 | 0.2 | 0.2 | 0.2 | 0.2 |
| Hydrated silicon dioxide | | 0.5 | 0.5 | 0.5 | 0.5 | 0.5 | 0.5 | 0.5 | 0.5 | 0.5 | 0.5 | 0.5 | 0.5 | 0.5 | 0.5 | 0.5 |
| Total | | 100.0 | 100.0 | 100.0 | 100.0 | 100.0 | 100.0 | 100.0 | 100.0 | 100.0 | 100.0 | 100.0 | 100.0 | 100.0 | 100.0 | 100.0 |
| Crospovidone ratio in disintegrant (%) | | 0.0 | 33.3 | 46.7 | 73.3 | 100.0 | 0.0 | 33.3 | 46.7 | 73.3 | 100.0 | 0.0 | 33.3 | 46.7 | 73.3 | 100.0 |
| AA content (mg) | | 300.0 | 300.0 | 300.0 | 300.0 | 300.0 | 300.0 | 300.0 | 300.0 | 300.0 | 300.0 | 300.0 | 300.0 | 300.0 | 300.0 | 300.0 |
| Diameter of tablet (mm) | | 9 | 9 | 9 | 9 | 9 | 9 | 9 | 9 | 9 | 9 | 9 | 9 | 9 | 9 | 9 |
| Thickness of tablet (mm) | | 4.5 | 4.5 | 4.5 | 4.5 | 4.5 | 4.8 | 4.8 | 4.8 | 4.8 | 4.8 | 5.4 | 5.4 | 5.4 | 5.4 | 5.4 |
| Weight of tablet (mg) | | 333 | 333 | 333 | 333 | 333 | 333 | 333 | 333 | 333 | 333 | 333 | 333 | 333 | 333 | 333 |
| Tablet hardness (N) | | 74 | 60 | 60 | 60 | 61 | 68 | 61 | 60 | 60 | 66 | 69 | 74 | 67 | 74 | 62 |
| 15-minute dissolution rate (%) | | 71 | 89 | 99 | 82 | 79 | 50 | 76 | 67 | 51 | 53 | 65 | 55 | 51 | 56 | 61 |

API: active pharmaceutical ingredient

The tablets 11 and 12 indicated in Table 6 were manufactured using croscarmellose sodium or sodium starch glycolate in place of crospovidone. All of the tablets referenced in Table 6 could be direct compression tableted. The dissolution test was also performed on the tablets. The compositions and properties of the tablets are given in Table 6.

TABLE 6

| | | Tablet name | Tablet 11 | Tablet 12 |
|---|---|---|---|---|
| Composition (%) | | AA API a | 90.0 | 90.0 |
| | Dis-integrant | Croscarmellose sodium | 0.7 | — |
| | | Sodium starch glycolate | — | 0.7 |
| | | Low-substituted hydroxypropyl cellulose | 0.8 | 0.8 |
| | | Crystalline cellulose | 7.8 | 7.8 |
| | | Magnesium stearate | 0.2 | 0.2 |
| | | Hydrated silicon dioxide | 0.5 | 0.5 |
| | | Total | 100.0 | 100.0 |
| Characteristics | | AA content (mg) | 300.0 | 300.0 |
| | | Diameter of tablet (mm) | 9 | 9 |
| | | Thickness of tablet (mm) | 4.5 | 4.5 |
| | | Weight of tablet (mg) | 333 | 333 |
| | | Tablet hardness (N) | 63 | 59 |
| | | 15-minute dissolution rate (%) | 94 | 96 |

API: active pharmaceutical ingredient

The tablets manufactured using croscarmellose sodium or sodium starch glycolate rather than crospovidone could be direct compression tableted and satisfied the dissolution rate standard.

Example 7: Examination of the Disintegrant Content

Tablets were manufactured using AA active pharmaceutical ingredient f or g and using the compositions indicated in Table 7. Tablets F1 to F4 in Table 7 were manufactured using active pharmaceutical ingredient f with the total amount of the two disintegrants being varied between 1.0% and 3.0%. The tablet G was manufactured using active pharmaceutical ingredient g and using 3.0% for the total amount of the two disintegrants. All of the tablets indicated in Table 7 could be direct compression tableted. The dissolution test was also performed on the tablets. The compositions and properties of the tablets are given in Table 7.

TABLE 7

| | | | Tablet F1 | Tablet F2 | Tablet F3 | Tablet F4 | Tablet G |
|---|---|---|---|---|---|---|---|
| Composition (%) | AA API f | | 90.0 | 88.0 | 88.0 | 88.0 | — |
| | AA API g | | — | — | — | — | 88.0 |
| | Dis-integrant | Crospovidone | 0.5 | 1.2 | 0.8 | 1.3 | 1.3 |
| | | Low-substituted hydroxypropyl cellulose | 0.9 | 1.6 | 1.2 | 1.7 | 1.7 |
| | | Crystalline cellulose | 7.9 | 8.5 | 9.3 | 8.3 | 8.3 |
| | | Magnesium stearate | 0.2 | 0.2 | 0.2 | 0.2 | 0.2 |
| | | Hydrated silicon dioxide | 0.5 | 0.5 | 0.5 | 0.5 | 0.5 |
| | | Crospovidone ratio in disintegrant (%) | 35.7 | 42.9 | 40.0 | 43.3 | 43.3 |
| | | Total | 100.0 | 100.0 | 100.0 | 100.0 | 100.0 |
| Characteristics | | AA content (mg) | 300.0 | 300.0 | 300.0 | 300.0 | 300.0 |
| | | Diameter of tablet (mm) | 9 | 9 | 9 | 9 | 9 |
| | | Thickness of tablet (mm) | 4.5 | 4.6 | 4.6 | 4.6 | 4.6 |
| | | Weight of tablet (mg) | 333 | 333 | 333 | 333 | 333 |
| | | Tablet hardness (N) | 68 | 67 | 57 | 60 | 59 |
| | | 15-minute dissolution rate (%) | 91 | 99 | 97 | 97 | 98 |

API: active pharmaceutical ingredient

All of the tablets indicated in Table 7 could be direct compression tableted and satisfied the dissolution rate standard.

The invention claimed is:

1. A tablet comprising:
acetaminophen that has a median particle diameter in a range from 100 to 350 μm;
crystalline cellulose that has a bulk density in a range from 0.10 to 0.23 g/cm$^3$; and
at least two types of disintegrants
wherein the at least two types of disintegrants are:
(a) at least one disintegrant selected from the group consisting of crospovidone, croscarmellose sodium, and sodium starch glycolate, and
(b) a disintegrant that is a low-substituted hydroxypropyl cellulose;
wherein the ratio of disintegrant (a) in the total of disintegrants (a) and (b) is 30 to 90 weight percent,
wherein the acetaminophen content per tablet is at least 86 weight %;
wherein the crystalline cellulose content in each tablet is at least 7.3 weight % and not more than 12 weight %; and
wherein a total content of the disintegrants (a) and (b) in each tablet is 1.0 to 4.0 weight %.

2. The tablet according to claim 1, wherein the tablet hardness is at least 50 N.

3. The tablet according to claim 1, wherein an acetaminophen dissolution rate is at least 80% in 15 minutes.

4. A method for manufacturing the tablet according to claim 1, the method comprising:
obtaining a powder mixture by mixing acetaminophen that has a median particle diameter in a range from 100 to 350 m, crystalline cellulose that has a bulk density in a range from 0.10 to 0.23 g/cm$^3$, and at least two types of disintegrants; and
obtaining a tablet by direct compression tableting of the powder mixture, wherein the at least two types of disintegrants are:
- (a) at least one disintegrant selected from the group consisting of crospovidone, croscarmellose sodium, and sodium starch glycolate, and
- (b) a disintegrant that is a low-substituted hydroxypropyl cellulose;

wherein the ratio of disintegrant (a) in the total of disintegrants (a) and (b) is 30 to 90 weight percent, wherein the crystalline cellulose content in each tablet is in the range from 7.3 weight % to 12.0 weight %; and wherein a total content of the disintegrants (a) and (b) in each tablet is 1.0 to 4.0 weight %.

* * * * *